United States Patent
Lee et al.

(10) Patent No.: US 11,913,935 B2
(45) Date of Patent: Feb. 27, 2024

(54) METHOD FOR EVALUATING PROPERTIES OF POLYPROPYLENE RESIN, METHOD FOR PREPARING POLYPROPYLENE NON-WOVEN FABRIC, AND POLYPROPYLENE NON-WOVEN FABRIC

(71) Applicant: LG Chem, Ltd., Seoul (KR)

(72) Inventors: Hyunsup Lee, Daejeon (KR); Seong Min Chae, Daejeon (KR); Kyung Seop Noh, Daejeon (KR); Heekwang Park, Daejeon (KR); Ki Soo Lee, Daejeon (KR); Sangjin Jeon, Daejeon (KR); Myunghan Lee, Daejeon (KR)

(73) Assignee: LG Chem, Ltd. (KR)

( * ) Notice: Subject to any disclaimer, the term of this patent is extended or adjusted under 35 U.S.C. 154(b) by 527 days.

(21) Appl. No.: 17/059,724

(22) PCT Filed: Jun. 21, 2019

(86) PCT No.: PCT/KR2019/007542
§ 371 (c)(1),
(2) Date: Nov. 30, 2020

(87) PCT Pub. No.: WO2019/245338
PCT Pub. Date: Dec. 26, 2019

(65) Prior Publication Data
US 2021/0215661 A1    Jul. 15, 2021

(30) Foreign Application Priority Data
Jun. 22, 2018   (KR) .................. 10-2018-0072318

(51) Int. Cl.
*G01N 33/36* (2006.01)
*D04H 1/4291* (2012.01)
*D04H 1/56* (2006.01)
*D04H 3/007* (2012.01)

(52) U.S. Cl.
CPC ......... *G01N 33/367* (2013.01); *D04H 1/4291* (2013.01); *D04H 1/565* (2013.01); *D04H 3/007* (2013.01); *G01N 2203/0075* (2013.01)

(58) Field of Classification Search
CPC .............. G01N 33/36; G01N 33/367; G01N 2203/0075; G01N 3/00
See application file for complete search history.

(56) References Cited

U.S. PATENT DOCUMENTS

| 5,260,126 A | 11/1993 | Collier, IV et al. |
| 6,759,356 B1 | 7/2004 | Myers |
| 9,885,149 B2 | 2/2018 | Weeks et al. |
| 2004/0138379 A1 | 7/2004 | Wada et al. |
| 2005/0165173 A1 | 7/2005 | Autran et al. |
| 2007/0196637 A1* | 8/2007 | Good ................ C08J 5/043 428/297.4 |
| 2010/0024134 A1 | 2/2010 | Reid et al. |
| 2010/0190405 A1 | 7/2010 | Takebe et al. |
| 2015/0211160 A1 | 7/2015 | Hassan et al. |
| 2016/0152016 A1 | 6/2016 | Abe et al. |
| 2018/0038025 A1 | 2/2018 | Takaku et al. |
| 2019/0113428 A1 | 4/2019 | Lee et al. |

FOREIGN PATENT DOCUMENTS

| CN | 1513029 A | 7/2004 | |
| CN | 1646759 A | 7/2005 | |
| CN | 102575418 A | 7/2012 | |
| CN | 103068893 A | 4/2013 | |
| CN | 107407029 A | 11/2017 | |
| CN | 108883564 A | 11/2018 | |
| JP | S62-182629 A | 8/1987 | |
| JP | H08327515 A | 12/1996 | |
| JP | 2007-009403 A | 1/2007 | |
| JP | 2013-155476 A | 8/2013 | |
| JP | 2015-172111 A | 10/2015 | |
| JP | 2016118570 A | 6/2016 | |
| JP | 2017002423 A | 1/2017 | |
| JP | 2017505390 A | 2/2017 | |
| JP | 6339387 B2 | 6/2018 | |
| KR | 20070016109 A | 2/2007 | |
| KR | 20080103270 A | 11/2008 | |
| KR | 20170001384 A | 1/2017 | |
| KR | 20170029239 A | 3/2017 | |
| KR | 20180042024 A | 4/2018 | |
| WO | 9960060 A1 | 11/1999 | |
| WO | WO-2005121298 A1 * | 12/2005 | ......... C11D 17/0047 |
| WO | 2009026207 A1 | 2/2009 | |
| WO | 2018074732 A1 | 4/2018 | |
| WO | WO-2018074732 A1 * | 4/2018 | ............. B29C 49/78 |

OTHER PUBLICATIONS

Machine Translation of WO-2018074732-A1 (Year: 2018).*
Search report from International Application No. PCT/KR2019/007542, dated Sep. 30, 2019.
Extended European Search Report for Application No. 19822797.7 dated Jun. 25, 2021. 7 pgs.

* cited by examiner

Primary Examiner — Nathaniel J Kolb

(74) *Attorney, Agent, or Firm* — Lerner David LLP

(57) ABSTRACT

The present invention relates to polypropylene non-woven fabric having excellent loft property, a method for preparing polypropylene non-woven fabric having excellent loft property, and a method for evaluating the properties of the polypropylene resin.

13 Claims, No Drawings

METHOD FOR EVALUATING PROPERTIES OF POLYPROPYLENE RESIN, METHOD FOR PREPARING POLYPROPYLENE NON-WOVEN FABRIC, AND POLYPROPYLENE NON-WOVEN FABRIC

CROSS-REFERENCE TO RELATED APPLICATIONS

This application is a national phase entry under 35 U.S.C. § 371 of International Application No. PCT/KR2019/007542 filed Jun. 21, 2019, which claims priority from Korean Patent Application No. 10-2018-0072318 filed Jun. 22, 2018, all of which are incorporated herein by reference.

TECHNICAL FIELD

The present invention relates to a method for evaluating the properties of polypropylene resin, a method for preparing polypropylene non-woven fabric, and polypropylene non-woven fabric.

BACKGROUND OF ART

Non-woven fabric or non-woven web is a fiber assembly of three-dimensional structure in which microfilaments having a diameter of about 10 μm are randomly entangled to form a spider web-like structure.

Since non-woven fabric or non-woven web is formed by bonding of microfilaments with each other, it has very excellent touch or feel, good processability, and excellent strength, softness and abrasion resistance.

Such non-woven fabric is being used for various applications in various technical fields, such as bandage materials, oil absorbers, building materials for sound absorption, disposable diapers, feminine hygienic products, and the like, and recently, is being widely used in the latest technical fields, such as dust protective clothing, dust protective mask, wiping cloth, micro filter, battery separator, and the like.

Although various processes of preparing non-woven fabric or non-woven web are known, among them, a melt blown process is used the most. In the melt blown process, thermoplastic plastic resin capable of forming filament yarn is discharged in a molten state through an orifice die including hundreds to thousands of orifices, high temperature gas is sprayed from the high speed gas spray holes positioned on both sides of the die to draw the filament yarn into micro fiber, and the micro fiber is deposited on a collector.

The prepared melt blown non-woven fabric can be used for various applications as described above, due to the structural characteristic wherein a micro fiber assembly is formed into a bulk structure.

In a common melt blown process, as plastic resin is discharged through an orifice die and drawn by high temperature gas, the diameter of filament yarn is determined, and it is largely influenced by the properties of plastic resin itself, as well as discharge pressure, gas temperature, and gas spray speed.

Particularly, polypropylene non-woven fabric produced by the melt blown process is used for diapers, feminine hygienic products, fine dust masks, and the like, and in this case, because it directly contacts the skin of a user, high loft non-woven fabric having excellent flexibility and softness is required.

DETAILED DESCRIPTION OF THE INVENTION

Technical Problems

It is an object of the present invention to provide polypropylene non-woven fabric having excellent loft property.

It is another object of the present invention to provide a method for preparing polypropylene non-woven fabric having excellent loft property, and a method for evaluating the properties of the polypropylene resin.

Technical Solutions

A method for evaluating the properties of polypropylene resin is provided herein, which method comprises steps of:
applying 150 to 250% strain to a polypropylene sample;
a first time (Time S1) after applying the strain, measuring first residual stress (Stress S1);
a second time (Time S2) after applying the strain, measuring second residual stress (Stress S2); and
deriving a residual stress ratio represented by the following Equation 1:

$$\text{Residual stress ratio} = \text{Stress } S2/\text{Stress } S1 \quad \text{[Equation 1]}$$

in the Equation 1,
Stress S1 is first residual stress measured after the first time (Time S1),
Stress S2 is second residual stress measured after the second time (Time S2), and
Time S2>Time S1.

The steps of applying strain, and measuring the first and second residual stress may be progressed under temperature condition represented by the following Equation 2:

$$Tm \Leftarrow T < Td \quad \text{[Equation 2]}$$

in the Equation 2,
T is temperature condition under which the strain is applied,
Tm is the melting temperature of the polypropylene resin,
Td is a temperature at which the polypropylene sample begins to be thermally decomposed.

And, in the method for evaluating the properties of polypropylene resin, it is preferable that Time S1 may be 0.001 to 0.05 seconds, and Time S2 may be 0.1 to 5 seconds.

And, the method for evaluating the properties of polypropylene resin may be, specifically, for the evaluation and prediction of the loft property of polypropylene non-woven fabric prepared by a melt blown process.

For this purpose, the method for evaluating the properties of polypropylene resin may further comprise steps of: preparing a first polypropylene sample and a second polypropylene sample as the polypropylene sample; deriving residual stress ratios of the first and second polypropylene samples; and comparing the residual stress ratios of the first and second polypropylene samples.

Wherein, in case a difference between the residual stress ratios of the polypropylene samples as explained above is 10 times or more, it may be evaluated as being appropriate, and the polypropylene sample may include two or more kinds.

Meanwhile, a method for preparing polypropylene non-woven fabric is provided herein, which comprises steps of:
selecting first polypropylene resin and second polypropylene resin; and
simultaneously introducing the polypropylene resins into a melt blown process to prepare drawn yarns of the first and second polypropylene resins, wherein a difference between the residual stress ratios of the first and second propylene resins, respectively represented by the following Equation 1, is 10 times or more:

Residual stress ratio=Stress S2/Stress S1     [Equation 1]

in the Equation 1,

Stress S1 is first residual stress measured a first time (Time S1) after applying 150 to 250% strain to each of the first and second polypropylene resins, Stress S2 is second residual stress measured a second time (Time S2) after applying 150 to 250% strain to each of the first and second polypropylene resins, and Time S2>Time S1.

Wherein, the residual stress ratio may be measured under temperature condition represented by the following Equation 2.

$Tm \leftarrow T < Td$     [Equation 2]

in the Equation 2,

T is temperature condition under which the strain is applied,

Tm is the melting temperature of the polypropylene resin,

Td is a temperature at which the polypropylene sample begins to be thermally decomposed.

And, it may be preferable that the melt blown process is progressed under temperature condition of 150 to 250° C., and under 100 to 10,000 times length drawing condition.

The first and second polypropylene resins may respectively have weight average molecular weight of 10,000 to 250,000 g/mol, and molecular weight distribution value of 2 to 5.

Meanwhile, polypropylene non-woven fabric is provided herein, which comprises the drawn yarn of the first polypropylene resin and the drawn yarn of the second polypropylene resin, and a difference between the residual stress ratios of the first and second polypropylene resins, respectively represented by the following Equation 1, is 10 times or more:

Residual stress ratio=Stress S2/Stress S1     [Equation 1]

in the Equation 1,

Stress S1 is first residual stress measured a first time (Time S1) after applying 150 to 250% strain to each of the first and second polypropylene resins, Stress S2 is second residual stress measured a second time (Time S2) after applying 150 to 250% strain to each of the first and second polypropylene resins, and Time S2>Time 51.

Wherein, it may be preferable that the first and second polypropylene resins respectively have weight average molecular weight of 10,000 to 250,000 g/mol, and molecular weight distribution value of 2 to 5.

Advantageous Effects

According to the present invention, high loft polypropylene non-woven fabric having excellent flexibility and softness may be provided.

MODE OF THE INVENTION

One aspect of the present invention provides a method for evaluating the properties of polypropylene resin comprising steps of:

applying 150 to 250% strain to a polypropylene sample;

a first time (Time S1) after applying the strain, measuring first residual stress (Stress S1);

a second time (Time S2) after applying the strain, measuring second residual stress (Stress S2); and deriving a residual stress ratio represented by the following Equation 1:

Residual stress ratio=Stress S2/Stress S1     [Equation 1]

in the Equation 1,

Stress S1 is first residual stress measured after the first time (Time S1),

Stress S2 is second residual stress measured after the second time (Time S2), and Time S2>Time S1.

Another aspect of the present invention provides a method for preparing polypropylene non-woven fabric comprising steps of:

selecting a first polypropylene resin and a second polypropylene resin; and simultaneously introducing the polypropylene resins into a melt blown process to prepare drawn yarns of the first and second polypropylene resins, wherein a difference between the residual stress ratios of the first and second propylene resins, respectively represented by the following Equation 1, is 10 times or more:

Residual stress ratio=Stress S2/Stress S1     [Equation 1]

in the Equation 1,

Stress S1 is first residual stress measured a first time (Time S1) after applying 150 to 250% strain to each of the first and second polypropylene resins, Stress S2 is second residual stress measured a second time (Time S2) after applying 150 to 250% strain to each of the first and second polypropylene resins, and Time S2>Time S1.

Still another aspect of the present invention provides polypropylene non-woven fabric comprising drawn yarn of the first polypropylene resin and drawn yarn of the second polypropylene resin, and a difference between the residual stress ratios of the first and second polypropylene resins, respectively represented by the following Equation 1, is 10 times or more:

Residual stress ratio=Stress S2/Stress S1     [Equation 1]

in the Equation 1,

Stress S1 is first residual stress measured a first time (Time S1) after applying 150 to 250% strain to each of the first and second polypropylene resins, Stress S2 is second residual stress measured a second time (Time S2) after applying 150 to 250% strain to each of the first and second polypropylene resins, and Time S2>Time S1.

As used herein, terms "a first", "a second" and the like are used to explain various constructional elements, and they are used only to distinguish one constructional element from other constructional elements.

And, the terms used herein are only to explain specific embodiments, and are not intended to limit the present invention. A singular expression includes a plural expression thereof, unless it is expressly stated or obvious from the context that such is not intended. As used herein, the terms "comprise" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

And, in case it is stated that each layer or element is formed "on" or "above" each layer or element, it means that each layer or element is formed directly on each layer or element, or that other layers or elements may be additionally formed between the layers or on the object or substrate.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, the present invention will be explained in detail.

According to one aspect of the present invention, a method for evaluating the properties of polypropylene resin is provided, which comprises steps of:
applying 150 to 250% strain to a polypropylene sample;
a first time (Time S1) after applying the strain, measuring first residual stress (Stress S1);
a second time (Time S2) after applying the strain, measuring second residual stress (Stress S2); and
deriving a residual stress ratio represented by the following Equation 1:

$$\text{Residual stress ratio} = \text{Stress } S2/\text{Stress } S1 \qquad \text{[Equation 1]}$$

in the Equation 1,
Stress S1 is first residual stress measured after the first time (Time S1),
Stress S2 is second residual stress measured after the second time (Time S2), and
Time S2>Time S1.

The present inventors found out through the experiments that in the process of preparing non-woven fabric by introducing polypropylene resin into a melt blown process, the loft-related properties of the prepared polypropylene non-woven fabric are related to the properties of the polypropylene resin itself, and particularly, are highly related to a residual stress ratio that can be calculated from stress change according to time, after applying external force to a resin sample, and completed the present invention.

Specifically, the method for evaluating the properties of polypropylene resin comprises steps of:
applying 150 to 250% strain to a polypropylene sample;
a first time (Time S1) after applying the strain, measuring first residual stress (Stress S1);
a second time (Time S2) after applying the strain, measuring second residual stress (Stress S2); and
deriving a residual stress ratio represented by the following Equation 1:

$$\text{Residual stress ratio} = \text{Stress } S2/\text{Stress } S1 \qquad \text{[Equation 1]}$$

in the Equation 1,
Stress S1 is first residual stress measured after the first time (Time S1),
Stress S2 is second residual stress measured after the second time (Time S2), and
Time S2>Time S1.

Polymer resin such as polypropylene generates strain, which is appearance change by an external force, when an external force is applied, and such strain rapidly occurs, but stress relaxation is exhibited wherein residual stress in the resin slowly decreases and disappears as time elapses, and thus, residual stress appears in the form of a function of a time.

Namely, in case an external force is applied under specific temperature condition to generate strain in the shear direction and constantly maintain strain, stress relaxation by the movement of polymer resin itself is hardly generated, and thus, stress relaxation is generated by the relaxation of molecules at molecular level and viscous flow, and residual stress is reported as a function of time.

Thus, the method for evaluating the properties of polypropylene resin according to one aspect of the present invention quantifies residual stress ratio according to time while strain is maintained, after applying an external force to a resin specimen to generate strain.

Wherein, the step of applying strain, and the steps of measuring first and second residual stresses may be progressed under temperature condition represented by the following Equation 2.

$$Tm \Leftarrow T < Td \qquad \text{[Equation 2]}$$

in the Equation 2,
T is temperature condition under which the strain is applied,
Tm is the melting temperature of the polypropylene resin,
Td is a temperature at which the polypropylene sample begins to be thermally decomposed.

And, in the method for evaluating the properties of polypropylene resin, Time S1 may be about 0.001 to about 0.05 seconds, and Time S2 may be about 0.1 to about 5 seconds, and preferably Time S1 may be about 0.01 to about 0.03 seconds, or about 0.02 seconds, and Time S2 may be about 0.5 to about 2 seconds, or about 1 second. And, it is preferable that the value of Time S2/Time S1 is about 10 to about 100.

Namely, according to one embodiment of the present invention, in the stress relaxation experiment wherein an external force is applied to a polypropylene resin specimen to generate strain and stress is relaxed while the strain is maintained, residual stress in the resin specimen is measured, and through the ratio of the initial residual stress and residual stress after some time, the properties of polypropylene resin can be evaluated.

Specifically, the measurement of residual stress ratio of polypropylene and evaluation of the properties may be for the evaluation and prediction of loft property of polypropylene non-woven fabric, when the polypropylene resin is introduced into a melt blown process to prepare polypropylene non-woven fabric.

For this purpose, the method for evaluating the properties of polypropylene may be conducted by preparing two or more kinds of polypropylene samples, measuring each residual stress ratio, and comparing them.

Specifically, for example, the method for evaluating the properties of polypropylene may comprise steps of preparing a first polypropylene sample and a second polypropylene sample as the polypropylene sample. Namely, two or more kinds of polypropylene samples are prepared, and the first and second polypropylene samples may be identical to or different from each other.

And, each residual stress ratio of the first and second polypropylene samples can be derived. A specific method of deriving each residual stress ratio is explained in the above, and the like.

Thereafter, the residual stress ratios of the first and second polypropylene samples are compared.

Wherein, in case a difference between the residual stress ratios of polypropylene samples as explained above is 10 times or more, or 10 times to about 100 times, or about 10 times to about 20 times, it may be evaluated as being appropriate. Namely, in case a difference between residual stress ratios of polypropylene samples is over a certain level, polypropylene non-woven fabric prepared by respectively introducing corresponding two kinds of polypropylene resins into a melt blown process may have very excellent loft property.

And, the polypropylene sample is not necessarily limited to two kinds, but may include 3 or more kinds, and in this case, if a difference between residual stress ratios of any one pair of polypropylene samples among the total polypropylene samples is 10 times or more, it is considered as fulfilling the requirement of the present invention.

Meanwhile, a method for preparing polypropylene non-woven fabric is provided, which comprises steps of:
selecting first polypropylene resin and second polypropylene resin; and
simultaneously introducing the polypropylene resins into a melt blown process to prepare drawn yarns of the first and second polypropylene resins,
wherein a difference between the residual stress ratios of the first and second propylene resins, respectively represented by the following Equation 1, is 10 times or more:

$$\text{Residual stress ratio} = \text{Stress } S2/\text{Stress } S1 \quad \text{[Equation 1]}$$

in the Equation 1,
Stress S1 is first residual stress measured a first time (Time S1) after applying 150 to 250% strain to each of the first and second polypropylene resins,
Stress S2 is second residual stress measured a second time (Time S2) after applying 150 to 250% strain to each of the first and second polypropylene resins, and
Time S2>Time S1.

Namely, the method for preparing polypropylene non-woven fabric according to another aspect of the present invention is identical to the existing method for preparing polypropylene non-woven fabric, except that the polypropylene resin raw materials introduced into a melt blown process is selected according to specific conditions.

The melt blown process may be progressed under temperature condition of about 150 to about 250° C., preferably about 170° C. or about 230° C.

And, the melt blown process may be progressed at a draw ratio of about 100 to about 10,000 times, preferably about 100 to about 1,500 times, or about 200 to about 1,200 times.

And, the drawing speed may be about 1,000 to about 100,000 times/s, preferably about 1000 to about 15,000 times/s, or about 200 to about 1,200 times/s.

However, the present invention is not necessarily limited to the above process conditions, and the process conditions may be determined according to the melting property of polypropylene resin to be processed.

And, the raw material resins of the melt blown process, the first and second polypropylene resins may respectively have weight average molecular weight of about 10,000 to about 250,000 g/mol. And, each molecular weight distribution value may be about 2 to about 5. The molecular weight-related properties of the polypropylene resin may be measured through GPC using polystyrene having molecular weight of 20,000 g/mol as a standard.

Meanwhile, polypropylene non-woven fabric is provided herein, which comprises drawn yarn of the first polypropylene resin and drawn yarn of the second polypropylene resin,
wherein a difference between the residual stress ratios of the first and second polypropylene resins, respectively represented by the following Equation 1, is 10 times or more:

$$\text{Residual stress ratio} = \text{Stress } S2/\text{Stress } S1 \quad \text{[Equation 1]}$$

in the Equation 1,
Stress S1 is first residual stress measured a first time (Time S1) after applying 150 to 250% strain to each of the first and second polypropylene resins,
Stress S2 is second residual stress measured a second time (Time S2) after applying 150 to 250% strain to each of the first and second polypropylene resins, and
Time S2>Time S1.

The polypropylene non-woven fabric according to another aspect of the present invention is prepared using two or more kinds of polypropylene resins having different residual stress ratios.

In the process of processing polymer resin such as propylene into a product such as non-woven fabric, strain of predetermined rate is intentionally generated by an external force to process into drawn yarn.

Inside of the polymer resin strained by an external force, the above explained residual stress exists, and shrinkage may be generated for the relaxation of the residual stress, and if the residual stress ratio is higher, shrinkage is generated more.

In the process of preparing drawn yarn, if two or more kinds polypropylene resins having different residual stress ratios are used, the resin having higher residual stress ratio is shrunken relatively more, and the resin having lower residual stress ratio is shrunken relatively less, thereby generating bending of drawn yarn by the difference in shrinkage ratio.

Thus, polypropylene non-woven fabric prepared using two or more kinds of polypropylene resins having different residual stress ratios includes highly bended, rolled, curled yarn, and it may have properties relating to excellent loft such as flexibility, softness, abundance, and the like.

Wherein, the first and second polypropylene resins may respectively have weight average molecular weight of about 10,000 to about 250,000 g/mol, and molecular weight distribution value of about 2 o about 5. The molecular weight-related properties of polypropylene resin can be measured by GPC using polystyrene having molecular weight of 20,000 g/mol as a standard.

If the weight average molecular weight of each of the first and second polypropylene resins does not fall within the above range, processability may be deteriorated during the process of preparing non-woven fabric, and thus, cutting may be generated, or the surface of non-woven fabric may become rough and stiff, and particularly, if the weight average molecular weight is too small, the strength of non-woven fabric may be deteriorated.

Due to the above properties, the polypropylene non-woven fabric may have density of about 0.09 g/cm$^3$ or less, and preferably about 0.01 g/cm$^3$ or more, or about 0.03 g/cm$^3$ or more, or about 0.05 g/cm$^3$ or more, or about 0.07 g/cm$^3$ or more, and preferably about 0.09 g/cm$^3$ or less, or about 0.087 g/cm$^3$ or less, or about 0.085 g/cm$^3$ or less, or 0.083 g/cm$^3$ or less.

Hereinafter, the actions and effects of the invention will be explained in more detail through specific examples. However, there examples are presented only as the illustrations of the invention, and the scope of the right of the invention is not determined thereby.

EXAMPLE

Preparation of Polypropylene Resin

Polypropylene resin having the property values of the following Table 1 was dried in a 40° C. vacuum oven overnight, and prepared in the form of pellets using a twin screw extruder, BA-19 (manufacturing company: BAU-TECH).

The pellet-shaped resin obtained by extrusion was dried again in a 40° C. vacuum oven overnight, and then, using Xplore 5.cc micro injection molding machine, prepared into specimens in the forms suitable for each property measurement condition.

1) Measurement of Molecular Weight Properties

The molecular weight properties of the prepared polypropylene resin was measured by GPC/SEC using polystyrene (Mw:20,000) as a standard.

2) Measurement of Viscosity

Viscosity was measured using Discovery Hybrid Rheometer of TA Instruments.

First, a polypropylene pellet was loaded on the circular lower plate of the above instrument, dissolved at about 235° C., and then, pressed with the upper plate, thereby measuring viscosity while maintaining a gap between the upper-lower plates at 1 mm. The measurement was progressed in the linear region where there is no change in viscosity and modulus according to strain change.

3) Measurement of Residual Stress Ratio

The measurement was progressed using Discovery Hybrid Rheometer of TA Instruments.

First, a polypropylene pellet was loaded on the circular lower plate of the above instrument, dissolved at about 235° C., and then, pressed with the upper plate, thus maintaining a gap between the upper-lower plates at 1 mm.

Thereafter, 200% strain was added thereto, and while maintaining the strain, residual stress according to time was measured.

Temperature: 235° C.

Strain: 200%

Measurement of residual stress (Stress S1): An external force was applied to generate 200% strain, and then, while maintaining the strain, residual stress was measured after 0.02 seconds (Time S1).

Measurement of residual stress (Stress S2): An external force was applied to generate 200% strain, and then, while maintaining the strain, residual stress was measured after 1 second (Time S2).

Time $S2$/Time $S1$=50

Residual stress ratio=calculated as % by Stress $S2$/Stress $S1$

The measurement results were summarized in the following Table 1.

TABLE 1

|  | Weight average molecular weight (g/mol) | Molecular weight distribution (Mw/Mn) | Viscosity (1 Hz, Pa·s) | Residual stress ratio (%) |
|---|---|---|---|---|
| Preparation Example 1 | 143,000 | 2.90 | 159 | 0.0051 |

TABLE 1-continued

|  | Weight average molecular weight (g/mol) | Molecular weight distribution (Mw/Mn) | Viscosity (1 Hz, Pa·s) | Residual stress ratio (%) |
|---|---|---|---|---|
| Preparation Example 2 | 176,000 | 2.35 | 315 | 0.0245 |
| Preparation Example 3 | 184,000 | 2.81 | 315 | 0.0430 |
| Preparation Example 4 | — | — | 311 | 0.0542 |
| Preparation Example 5 | 182,000 | 4.8 | 329 | 0.0627 |

*The polypropylene resin of Preparation Example 4 was prepared by mixing the polypropylene resins of Preparation Example 2 and Preparation Example 5 at a weight ratio of 7:3.

Preparation of Polypropylene Non-Woven Fabric

Polypropylene non-woven fabric was prepared using equipment of Reifenhauser Company.

As summarized in the following Table 2, two kinds of polypropylene resins were prepared, and respectively introduced into an extruder. The introduced polypropylene resin was combined in an outlet and spun.

The spun polypropylene filament was solidified by cooling air sprayed through the chamber, drawn by the pressure of the air blown at the top and the air inhaled at the bottom of the conveyer belt, deposited on the conveyer belt to form a web, and then, thermally bonded to prepare non-woven fabric.

Measurement of Density of Non-Woven Fabric

For the non-woven fabric prepared by the above method, density was measured.

The measurement results were summarized in the following Table 2.

TABLE 2

|  | Polypropylene resin | Residual stress difference (times) | Relevance assessment | Density (g/cm³) |
|---|---|---|---|---|
| Example 1 | Preparation Examples 1 and 2 | 4.78 | X | 0.095 |
| Example 2 | Preparation Examples 1 and 3 | 8.41 | X | 0.091 |
| Example 3 | Preparation Examples 1 and 4 | 10.59 | O | 0.082 |
| Example 4 | Preparation Examples 1 and 5 | 12.24 | O | 0.077 |

Referring to the Table 2, it can be seen that in case non-woven fabric is prepared using two kinds of polypropylene resins having specific residual stress ratio difference according to one example of the present invention, even if prepared by the same process, it has relatively low density.

Specifically, it can be clearly confirmed that in case polypropylene resins having residual stress ratio difference of 10 times or more is used according to the examples of the present invention, the density of the non-woven fabric is in the range of about 0.07 to about 0.085 g/cm3, while in case polypropylene resins having small residual stress ratio difference is used, the density is about 0.091 g/cm3 or more.

Such a difference in density is interpreted as arising from the increased content of highly bended, rolled, curled-yarn of polypropylene drawn yarn, by using two or more kinds of polypropylene resins having different residual stress ratios in the process of preparing drawn yarn, and thus, it can be predicted that the polypropylene non-woven fabric according to one example of the present invention has excellent loft-related properties such as flexibility, softness, abundance, and the like.

And, referring to Table 2, it can be clearly seen that the relevance assessment through residual stress ratio difference according to the examples of the present invention corresponds with the tendency of density of practically prepared non-woven fabric.

Thus, it can be seen that according to the present invention, a polypropylene resin sample suitable for the preparation of non-woven fabric can be easily selected through Lab scale property measurement of polypropylene resin specimens.

The invention claimed is:

1. A method for evaluating a loft property of a propylene non-woven fabric prepared by a melt blown process of a combination of a first polypropylene resin and a second polypropylene resin, the method comprising steps of:
   preparing a first sample of the first polypropylene resin and preparing a second sample of the second polypropylene resin, respectively;
   deriving a residual stress ratio of the first sample and a residual stress ratio of the second sample, respectively, by the steps of:
      applying 150 to 250% strain to each sample;
      a first time (Time S1) after applying the strain, measuring a first residual stress (Stress S1);
      a second time (Time S2) after applying the strain, measuring a second residual stress (Stress S2); and
      deriving a residual stress ratio represented by Equation 1:

Residual stress ratio=Stress $S2$/Stress $S1$     [Equation 1]

in Equation 1,
   Stress S1 is the first residual stress measured after the first time (Time S1),
   Stress S2 is the second residual stress measured after the second time (Time S2), and
   Time S2>Time S1,
   comparing the residual stress ratio of the first sample and the residual stress ratio of the second sample, and
   determining that the loft property of the propylene non-woven fabric is appropriate if the residual stress ratio of the first sample is at least 10 times the residual stress ratio of the second sample.

2. The method for evaluating a loft property of a propylene non-woven fabric according to claim 1, wherein the steps of applying strain, and measuring the first and second residual stress are progressed under a temperature condition represented by Equation 2:

$Tm \Leftarrow T < Td$     [Equation 2]

in Equation 2,
   T is the temperature condition under which the strain is applied,
   Tm is the melting temperature of each sample,
   Td is a temperature at which each sample begins to be thermally decomposed.

3. The method for evaluating a loft property of a propylene non-woven fabric according to claim 1, wherein Time S1 is 0.001 to 0.05 seconds, and Time S2 is 0.1 to 5 seconds.

4. A method for preparing a polypropylene non-woven fabric comprising steps of:
   evaluating the loft property of the propylene non-woven fabric according to claim 1; and
   simultaneously introducing the first and second polypropylene resins into a melt blown process to prepare drawn yarns of the first and second polypropylene resins.

5. The method for preparing a polypropylene non-woven fabric according to claim 4, wherein the residual stress ratio is measured under a temperature condition represented by Equation 2:

$Tm \Leftarrow T < Td$     [Equation 2]

in Equation 2,
   T is the temperature condition under which the strain is applied,
   Tm is the melting temperature of each sample, and
   Td is a temperature at which each sample begins to be thermally decomposed.

6. The method for preparing a polypropylene non-woven fabric according to claim 4, wherein the melt blown process is progressed under a temperature condition of 150 to 250° C.

7. The method for preparing a polypropylene non-woven fabric according to claim 4, wherein the melt blown process is progressed under 100 to 10,000 times length drawing condition.

8. The method for preparing a polypropylene non-woven fabric according to claim 4, wherein the first and second polypropylene resins respectively have a weight average molecular weight of 10,000 to 250,000 g/mol.

9. The method for preparing a polypropylene non-woven fabric according to claim 4, wherein the first and second polypropylene resins respectively have a molecular weight distribution value of 2 to 5.

10. A polypropylene non-woven fabric prepared according to the method of claim 4.

11. The polypropylene non-woven fabric according to claim 10, wherein the first and second polypropylene resins respectively have a weight average molecular weight of 10,000 to 250,000 g/mol.

12. The polypropylene non-woven fabric according to claim 10, wherein the first and second polypropylene resins respectively have a molecular weight distribution value of 2 to 5.

13. The polypropylene non-woven fabric according to claim 10, which has a density of 0.09 g/cm3 or less.

* * * * *